US006890310B2

(12) United States Patent
Fracavilla et al.

(10) Patent No.: US 6,890,310 B2
(45) Date of Patent: May 10, 2005

(54) ADAPTOR FOR USE WITH POINT-OF-CARE TESTING CARTRIDGE

(75) Inventors: Frank Fracavilla, Newton, NJ (US); Jamieson William Maclean Crawford, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 222 days.

(21) Appl. No.: 10/108,713

(22) Filed: Mar. 27, 2002

(65) Prior Publication Data

US 2002/0143274 A1 Oct. 3, 2002

Related U.S. Application Data

(60) Provisional application No. 60/280,430, filed on Mar. 30, 2001.

(51) Int. Cl.[7] ............................ A61B 5/00; B65D 81/00

(52) U.S. Cl. ....................... 600/573; 422/939; 206/364; 206/365

(58) Field of Search ................................ 600/573–576; 422/939–948; 206/364, 365

(56) References Cited

U.S. PATENT DOCUMENTS

| | | | | |
|---|---|---|---|---|
| 5,096,669 A | | 3/1992 | Lauks et al. | |
| 5,429,256 A | | 7/1995 | Kestenbaum | |
| 5,501,676 A | | 3/1996 | Niedospial et al. | |
| 5,611,785 A | | 3/1997 | Mito et al. | |
| 5,638,828 A | | 6/1997 | Lauks et al. | |
| 5,690,612 A | | 11/1997 | Lopez et al. | |
| 5,753,186 A | * | 5/1998 | Hanley et al. | 422/101 |
| 5,779,650 A | | 7/1998 | Lauks et al. | |
| 5,924,584 A | * | 7/1999 | Hellstrom et al. | 215/247 |
| 6,010,463 A | | 1/2000 | Lauks et al. | |
| 6,027,482 A | | 2/2000 | Imbert | |
| 6,213,597 B1 | | 4/2001 | Liu | |
| 6,350,254 B1 | | 2/2002 | Wilkinson et al. | |

* cited by examiner

*Primary Examiner*—Eric F. Winakur
*Assistant Examiner*—Jonathan Foreman

(57) ABSTRACT

An adaptor is provided to facilitate delivery of a fluid specimen from a syringe to a point-of-care testing cartridge. The adaptor includes a mounting sleeve for snapped engagement over a portion of the testing cartridge, including the entry port to the testing cartridge. The adaptor further includes a Luer fitting unitarily formed with the mounting sleeve. The Luer fitting has an inlet end configured for mating with the syringe and an outlet end configured for alignment with the entry port of the testing cartridge. The adaptor can be snapped onto the testing cartridge. The Luer tip of the syringe then can be mated with the Luer fitting of the adaptor for safe and convenient delivery of the specimen through the adaptor and into the testing cartridge.

9 Claims, 6 Drawing Sheets

ADAPTOR FOR USE WITH POINT-OF-CARE TESTING CARTRIDGE

RELATED APPLICATIONS

This application claims priority on U.S. Provisional Patent Appl. No. 60/280,430 filed on Mar. 30, 2001.

BACKGROUND OF THE INVENTION

1. Field of the Invention

The subject invention relates to an adaptor that can be snapped onto a point-of-care testing cartridge for facilitating the transfer of a specimen from a syringe to the testing cartridge.

2. Description of the Related Art

Many medical procedures require diagnostic tests to be performed on a sample of a patient's fluid. Fluid often is collected from a patient by employing a needle holder assembly and one or more evacuated tubes. Fluid also can be collected in a syringe. A syringe may be used with a metallic needle to obtain a fluid sample from a patient. However, syringes often are connected directly to an established arterial or venous line to obtain a fluid sample. The fluid collected in the syringe then may be transferred to a tube. The tubes are labeled carefully and shipped to a laboratory for analysis. The results of the laboratory analysis then are reported back to the health care provider. The results, of course, could be rushed in emergency situations, but absent an emergency would require more then one day between the time the sample is drawn from the patient to the time that the laboratory analysis is reported to the health care provider.

Devices have been developed for performing at least certain diagnostic tests on a sample of fluid at the point-of-care. The point-of-care diagnostic equipment includes a syringe for receiving a sample of fluid from a patient, a small disposable testing cartridge for receiving a portion of the fluid from the syringe and a portable clinical analyzer for analyzing the fluid and outputting the results. Combinations of testing cartridges and portable clinical analyzers are marketed in the United States by i-STAT Corporation, AVL Scientific Corporation and Diametrics Medical, Inc. The systems produced by these and other companies share certain common features. In particular, the testing cartridge of each system typically has a small rectangular housing about 1"×2" and about 0.25" thick. The housing includes an internal reservoir with a volume of between about 40 $\mu$l and 125 $\mu$l. An inlet port extends through an external wall of the testing cartridge and communicates with the internal reservoir. The cartridge further includes contact pads and sensors that can be placed in communication with the portable clinical analyzer. An example of an i-STAT point-of-care testing cartridge is shown in U.S. Pat. No. 5,638,828.

The prior art point-of-care testing systems are employed with a syringe that is used to draw a sample of fluid from a patient. The syringe then may be used to eject a portion of the fluid sample into the inlet port of the point-of-care testing cartridge. However, some testing cartridges are operative to automatically draw fluid from the syringe. The inlet port of the cartridge then is closed and the cartridge is placed in communication with the portable clinical analyzer for performing certain specified diagnostic tests on the sample of fluid in the cartridge. The analyzer then provides a very quick output of the test results without the need for sending the fluid sample to the laboratory.

Point-of-care testing systems provide several efficiencies over systems that require virtually all diagnostic tests to be performed at a location remote from the point-of-care. The small size of the testing cartridge facilitates storage and shipment of the cartridges while also contributing to the portability of the system. However, with regards to transferring a collected sample to the cartridge, the small cartridges can be very difficult to use. For example, alignment of the distal end of the syringe with the inlet port of the testing cartridge can be complicated and difficult. A misalignment or imprecise mating of the syringe with the inlet port of the testing cartridge can lead to a loss of a portion of the collected fluid sample. Additionally, it is difficult to use a syringe for accurately dispensing the proper volume of liquid. Too small a volume may prevent proper testing by the cartridge and the associated portable clinical analyzer. Too large a volume can cause splattering or spillage. Similarly an overfill can result in splatter when the cover of the point-of-care testing cartridge is closed. Fluid that is not delivered efficiently from the syringe into the inlet port of the testing cartridge create the potential for disease transmission. Similarly, a loss of fluid during the transfer from the syringe to the testing cartridge can leave an insufficient volume of fluid for performing the required diagnostic tests. An insufficient volume of fluid to perform the required tests can require the health care worker to return to the patient for a second sample of fluid. This is time consuming for the health care worker and traumatic for the patient. Additionally, some testing cartridges may require an insufficiently filled cartridge to be discarded and a new cartridge to be employed with the new sample of fluid. Thus, inefficiencies in the transfer of fluid from the syringe to the testing cartridge can generate excess costs for additional testing cartridges.

The direct transfer of fluid from a syringe to a testing cartridge can cause the syringe tip to close off the entry port and prevent venting of air from the testing cartridge. Thus bubbles are created. Bubbles reduce the volume of fluid and can affect test results.

SUMMARY OF THE INVENTION

The subject invention is directed to a snap on adaptor for use with a point-of-care testing cartridge and with a syringe assembly. The point-of-care testing cartridge may be a prior art testing cartridge as described above, or any yet-to-be developed testing cartridge for performing point-of-care diagnostic analysis on a collected specimen of blood or other bodily fluid. The testing cartridge comprises a housing having an internal reservoir for receiving a specimen to be tested. The housing may be substantially rectangular, with opposed top and bottom walls and a plurality of side walls. An entry port extends through the top wall and that communicates with the internal reservoir of the testing cartridge. The testing cartridge may further include contact pads and sensors that can be placed in communication with a portable clinical analyzer for performing point-of-care analysis of the collected specimen.

The syringe assembly that is used with the snap on adaptor may be a conventional prior art syringe assembly. The syringe assembly includes a body with opposed proximal and distal ends. A barrel extends distally from the proximal end of the body and defines a fluid receiving chamber that is widely open at the proximal end. A Luer tip projects from the barrel to the distal end of the syringe body and includes a passage that communicates with the fluid receiving chamber. The Luer tip includes a conically tapered outer surface that is dimensioned and configured for mating with the tapered proximal entry to the hub of a needle assembly or with the base of a plastic Luer fitting or a blunt plastic cannula. The distal end of the syringe body may further have an internally threaded Luer collar that projects from the distal end of the barrel and concentrically around the Luer tip. The threads of the Luer collar can be threadedly engaged with lugs at the proximal end of the hub of a needle assembly or with comparable lugs at the proximal end of a plastic Luer fitting blunt plastic cannula. Luer tips, Luer collars and mating structures on needles or cannulas are known in the art.

The syringe assembly further includes a plunger that is slidably received in the open proximal end of the fluid receiving chamber defined by the syringe barrel. Distal movement of the plunger in the fluid receiving chamber will expel a fluid from the chamber and through the Luer tip. Proximal movement of the plunger in the chamber will draw fluid through the Luer tip and into the chamber.

The syringe assembly with which the walled adaptor is used may further include a needle assembly, a plastic Luer fitting or a blunt plastic cannula for accessing blood or other bodily fluid to be tested. A conventional prior art needle assembly includes an elongate metallic needle cannula having a proximal end, a pointed distal end and a lumen extending between the ends. The prior art needle assembly further includes the plastic hub having opposed proximal and distal ends. The distal end of the hub is securely mounted to the proximal end of the needle cannula. The proximal end of the hub is configured for fluid-tight engagement with the Luer tip. Additionally, the proximal end of the hub may include lugs for threaded engagement with the internal threads on a Luer collar that may be present on the syringe. A plastic Luer fitting or a blunt plastic cannula typically is unitarily molded from a plastic material and has opposite proximal and distal ends and a lumen extending between the ends. The proximal end of the plastic Luer fitting or the blunt plastic cannula may have the same shape as the proximal end of the hub for the above-described needle assembly. The distal end of the blunt plastic cannula may be tapered sufficiently to pierce a septum across a fitting on an IV access system or blood collection set.

The snap on adaptor of the subject invention may be unitarily molded from a plastic material and comprises a mounting sleeve. The mounting sleeve includes a side wall for slidable engagement against a side wall of the testing cartridge, a bottom wall for slidable engagement against the bottom wall of the testing cartridge, a top wall for slidable engagement against portions of the top wall of the testing cartridge in proximity to the entry port and an end wall for positioning against an end wall of the testing cartridge. Inwardly facing surfaces of at least one of the side wall, bottom wall and top wall may be provided with detents for snapped engagement with structure on the testing cartridge.

The snap on adaptor further includes a Luer fitting with an inlet end, an outlet end and a passage extending between the ends. An inlet section extends from the inlet end toward the outlet end and is mounted to or incorporated into the top wall of the mounting sleeve. Portions of the passage of the Luer fitting that are disposed in the inlet section may be aligned substantially parallel to the top wall. Additionally, portions of the passage adjacent the inlet end are conically tapered and configured for secure fluid-tight engagement with a conventional Luer tip. In certain embodiments, the inlet end of the Luer fitting projects from the mounting sleeve, and is provided with a pair of lugs for threaded engagement with a Luer collar. The projection of the inlet end of the Luer fitting from the mounting sleeve is sufficient to prevent interference between the mounting sleeve and the Luer collar. The outlet end of the Luer fitting is disposed to register with the entry port of the testing cartridge. Additionally, portions of the passage of the Luer fitting adjacent the outlet end may be aligned substantially orthogonal to the top wall of the mounting sleeve and substantially orthogonal to portions of the passage adjacent the inlet end of the Luer fitting. Thus, the outlet portion of the passage may be substantially normal to the inlet portion of the passage. The outlet portion of the passage preferably is cross-sectionally smaller than the passage through the tip of the syringe. Thus, the rate of flow of fluid can be controlled precisely.

The adaptor may further include a cap for selectively closing the inlet end of the Luer fitting. The cap may be separable from the Luer fitting or tethered to portions of the adaptor in proximity to the inlet end of the Luer fitting.

The adaptor can be used by first drawing a specimen of blood or other bodily fluid with a syringe assembly substantially in a conventional manner. For example, the Luer tip of the syringe body or the blunt plastic cannula mounted to the Luer tip may be placed in communication with the fitting of an IV access system or blood collection set. Alternatively, a conventional needle assembly may be mounted to the Luer tip of the syringe body and the distal tip of the needle cannula can be inserted into a blood vessel of the patient or other source of bodily fluid to obtain the required specimen. With either of these approaches, fluid is drawn through the passage of the Luer tip and into the fluid receiving chamber of the syringe body by pulling the plunger of the syringe assembly in a proximal direction. Most point-of-care testing cartridges require between 40 $\mu$l and 125 $\mu$l to complete a test. Hence, the plunger of the syringe assembly is moved proximally to obtain a volume of fluid slightly in excess of the amount required by the particular testing cartridge that will be employed.

After the appropriate volume of fluid has been collected, the needle assembly, if used, is removed in an accepted safe manner and deposited in a sharps receptacle. Alternatively, any plastic Luer fitting or blunt plastic cannula that may have been mounted to the distal end of the syringe body is removed and discarded into a sharps receptacle in a conventional accepted safe manner.

The point-of-care testing cartridge then is removed from the manufacturer's package. Many manufacturers of testing cartridges provide a cover for the inlet port that is hinged into a covering disposition over the inlet port both prior to and after deposition of blood sample into the testing cartridge. Thus, a cover, if present on the testing cartridge, must be rotated away from the inlet port of the testing cartridge. The mounting sleeve of the adaptor then is slid onto the testing cartridge sufficiently for the detents on the mounting sleeve to engage corresponding structure on outer surfaces of the testing cartridge. In the fully mounted condition, the outlet end of the passage through the Luer fitting will register with the entry port of the adaptor. A cap, if any, that had been mounted to the inlet end of the adaptor then may be removed and maintained in an available position. The tip of the syringe then is placed in communication with the inlet end of the Luer fitting. This may involve mere slidable insertion of a Luer tip into the conically tapered portions of the passage adjacent the inlet end to achieve a fluid-tight frictional interfit. Alternatively, lugs at the inlet end of the Luer fitting can be threaded into engagement with a conventional Luer collar, thereby simultaneously urging the Luer tip of the syringe into engagement with the inlet end of the passage. The plunger of the syringe assembly then is moved distally to urge a selected volume of the specimen from the fluid receiving chamber of the syringe body, through the adaptor and into the testing cartridge. The syringe assembly then is removed from the testing cartridge and is discarded in a conventional safe manner. The cap of the adaptor then is sealingly engaged over the inlet end of the cartridge, and the testing cartridge is presented to a portable clinical analyzer substantially in the conventional manner. Alternatively, the testing cartridge may be connected to the portable clinical analyzer before the specimen is deposited in the testing cartridge.

DETAILED DESCRIPTION

A snap on adaptor in accordance with the subject invention is identified generally by the numeral 10 in FIGS. 1–4. Adaptor 10 is used with a syringe assembly 12, as shown most clearly in FIG. 5, and with a point-of-care testing cartridge 14, as shown most clearly in FIG. 6.

Figure 1:
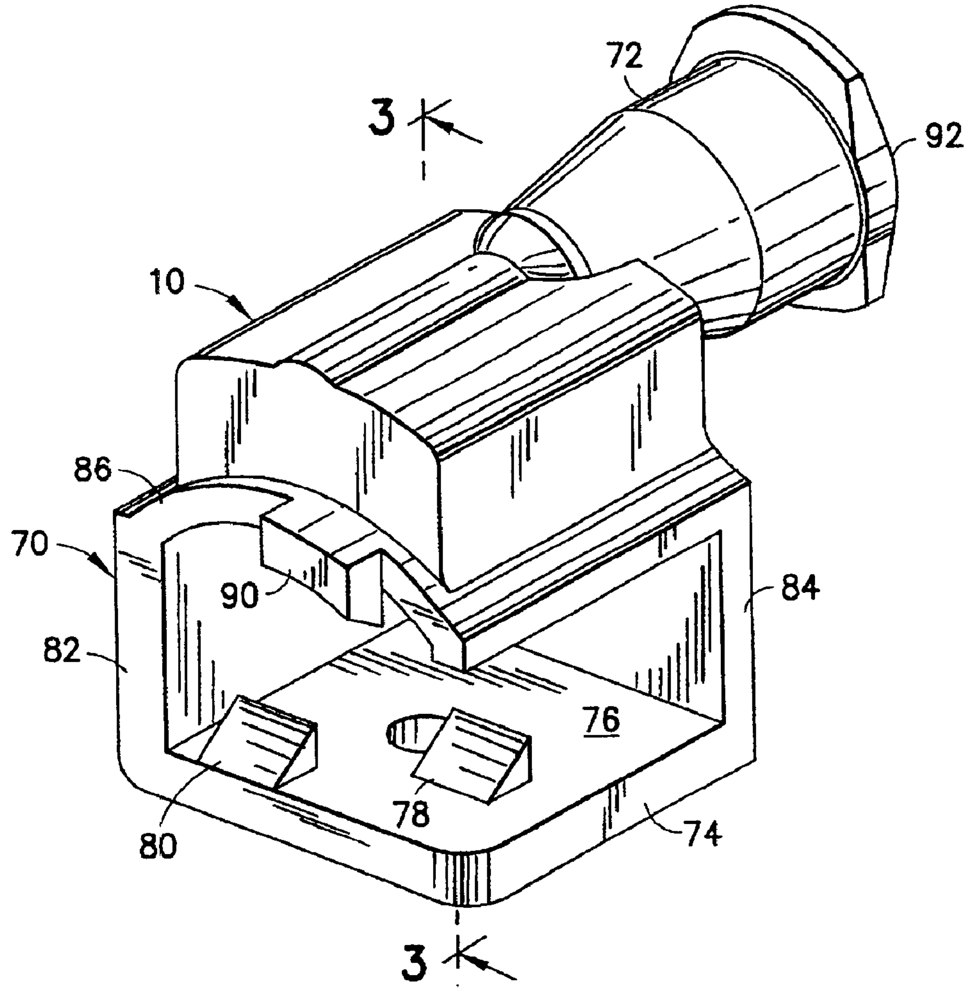
FIG. 1 is a perspective view of an adaptor in accordance with the subject invention as viewed from the top.
Figure 2:
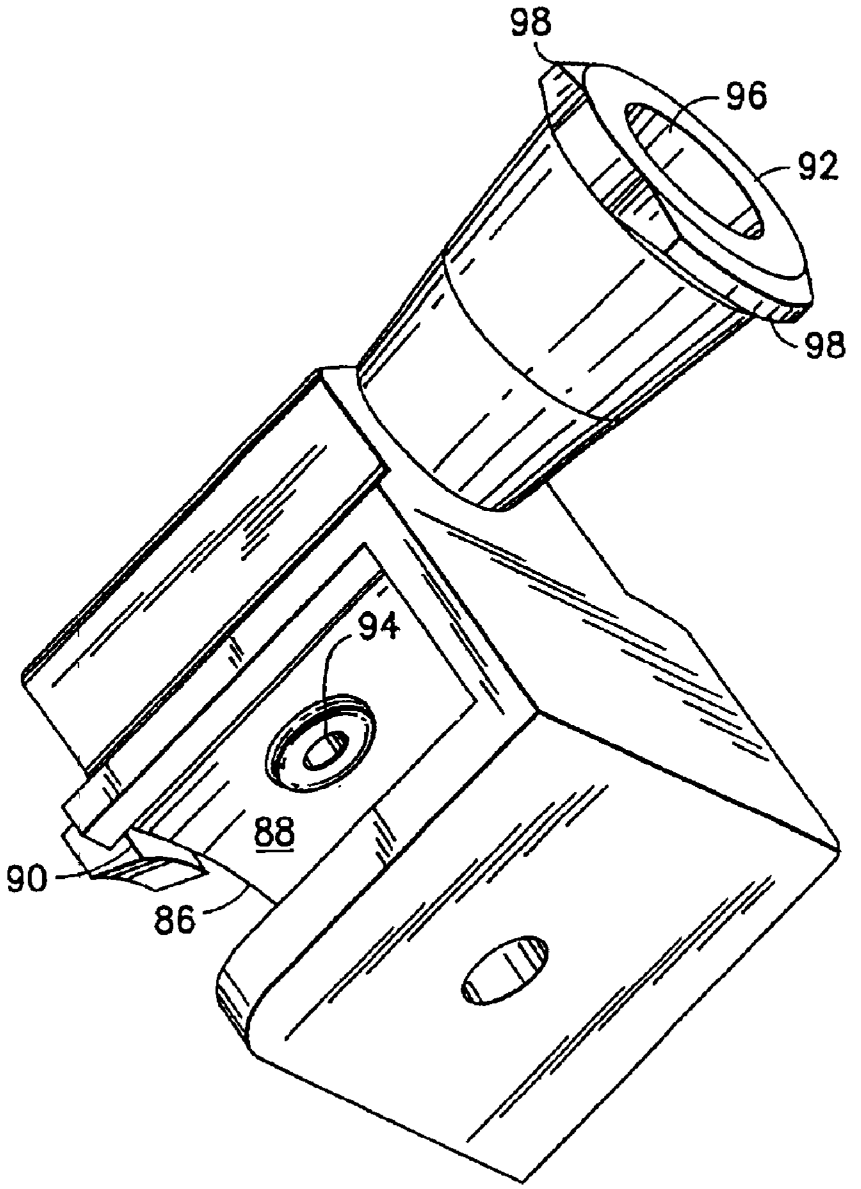
FIG. 2 is a perspective view of the adaptor as viewed from the bottom.
Figure 3:
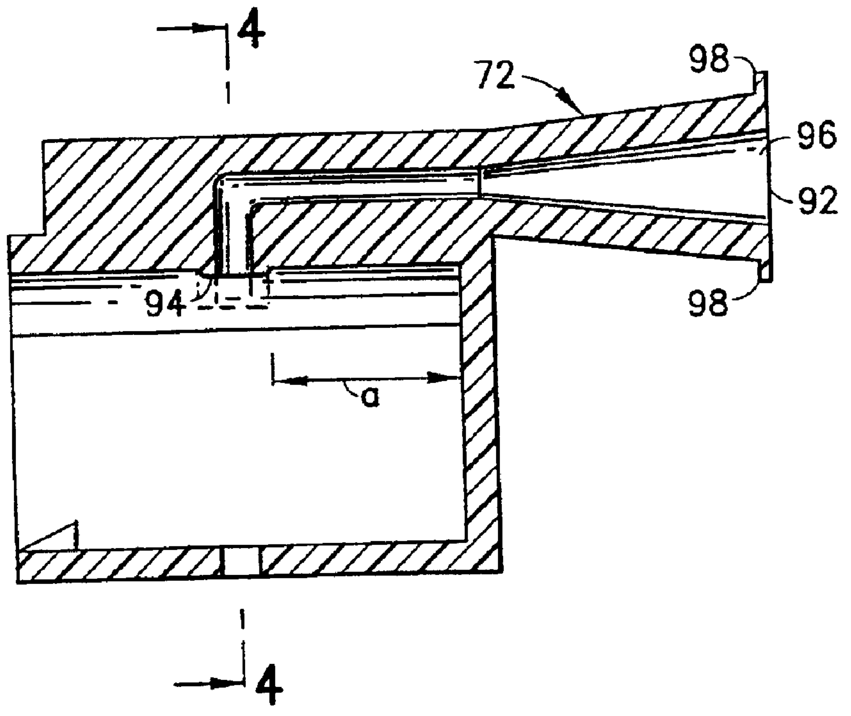
FIG. 3 is a cross-sectional view taken along line 3—3 in FIG. 1.
Figure 4:
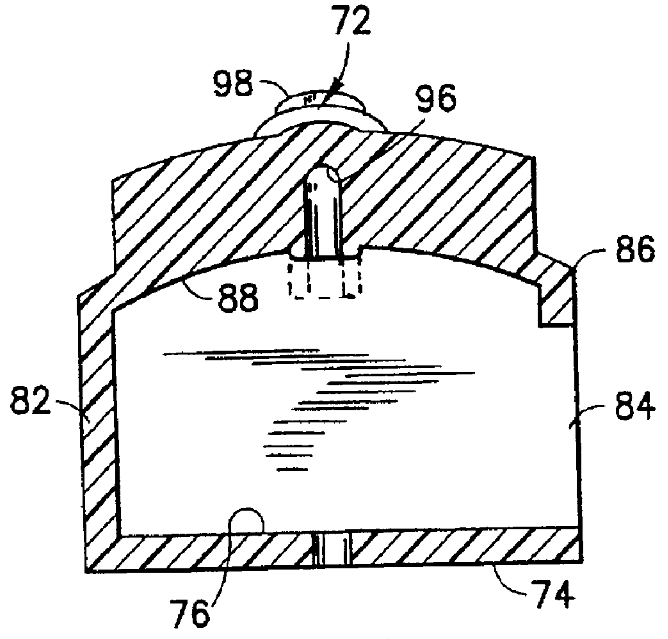
FIG. 4 is a cross-sectional view taken along line 4—4 in FIG. 3.
Figure 5:
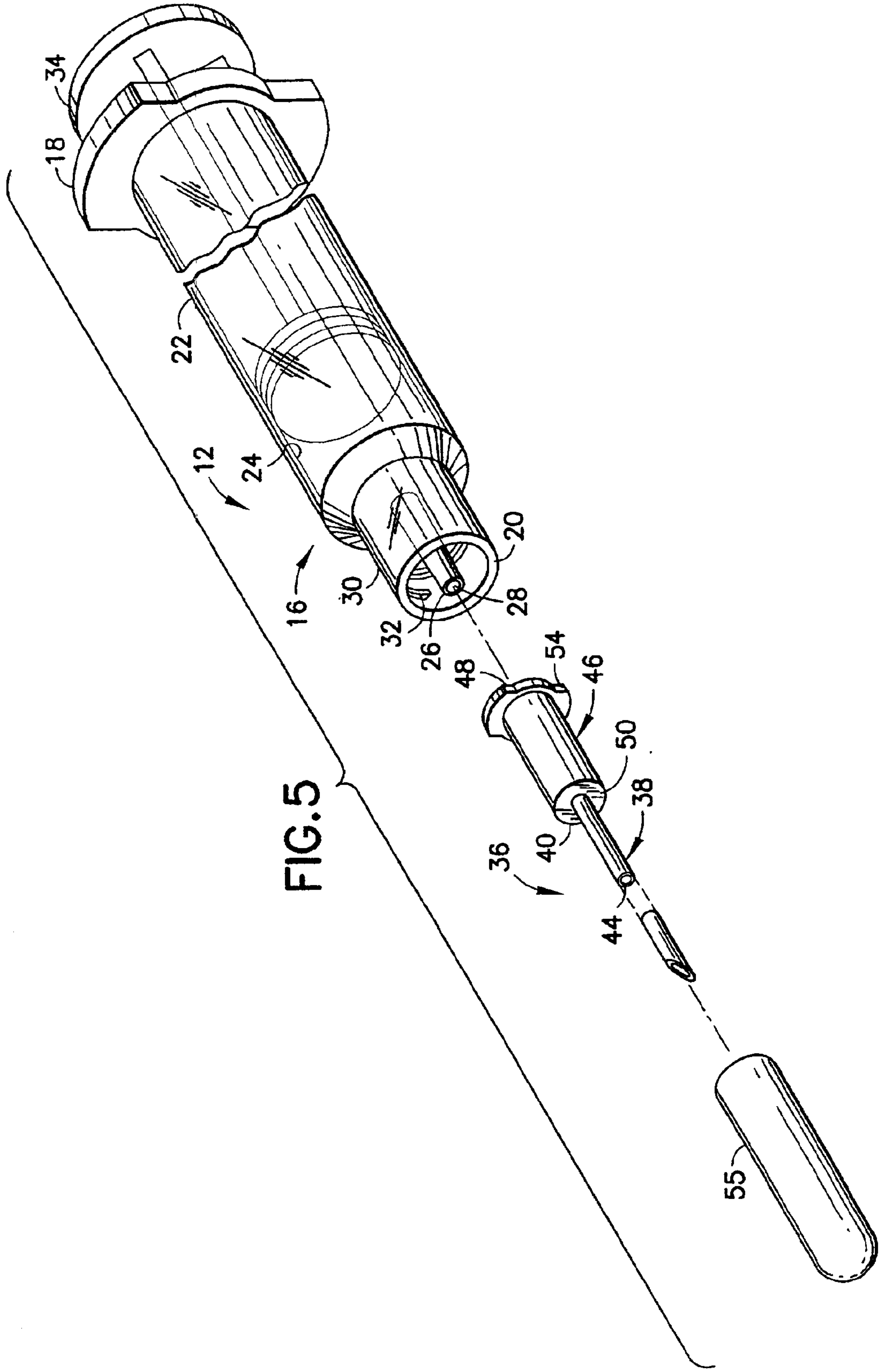
FIG. 5 is a perspective view of a syringe for use with the adaptor shown in FIGS. 1–4.

Syringe assembly 12, as shown in FIG. 5, includes a syringe body 16 having a proximal end 18 and a distal end 20. A barrel 22 extends distally from proximal end 18 and defines a cylindrical fluid receiving chamber 24 that is widely open at proximal end 18. A frustoconically tapered tip 26 extends from barrel 22 to distal end 20 of syringe body 16. Tip 26 is provided with a narrow cylindrical passage 28 that communicates with fluid receiving chamber 24 of barrel 22. An optional Luer collar 30 projects distally from barrel 22 and concentrically surrounds tip 26. Luer collar 30 is provided with an internal array of threads 32. Syringe assembly 12 further includes a plunger 34 slideably disposed in fluid receiving chamber 24 and in fluid-tight engagement with the cylindrical walls of chamber 22. Plunger 34 can be moved alternately in proximal or distal directions for urging fluid through passage 28 in tip 26 and into or out of fluid receiving chamber 24.

Syringe assembly 12 optionally includes a needle assembly 36. Needle assembly 36 includes a metallic needle cannula 38 having a proximal end 40, a sharply pointed distal end 42 and a lumen 44 extending between the ends. Needle assembly 36 further includes a hub 46 that has a proximal end 48, a distal end 50 and a passage extending therebetween. Distal end 50 of hub 46 is securely mounted to proximal end 40 of needle cannula 38 such that the passage through hub 46 communicates with lumen 44 through needle cannula 38. The passage of hub 46 defines a taper that substantially matches tapered distal tip 26 on syringe body 16. Thus, tapered tip 26 of syringe body 16 can be placed in fluid-tight frictional engagement with the passage in proximal end 48 of hub 46. Proximal end 48 of hub 46 is further characterized by a pair of diametrically opposite lugs 54 that are dimensioned and configured for engagement with threads 32 of Luer collar 31D. Thus, lumen 44 through needle cannula 38 can be placed in communication with passage 28 in tip 26 and with fluid receiving chamber 24 of syringe body 16. Needle assembly 36 further includes a protective cap 55 removably engaged over needle cannula 38.

Figure 6:
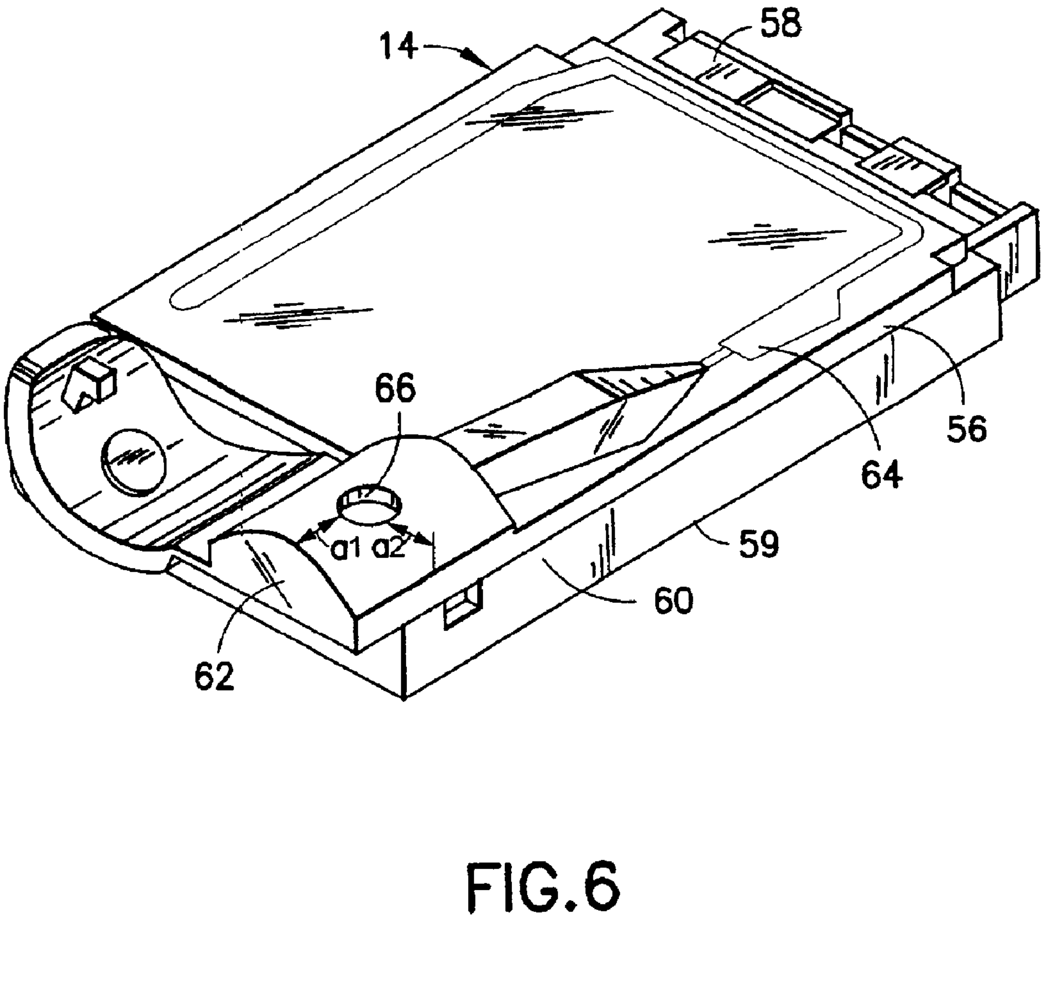
FIG. 6 is a perspective view of a testing cartridge for use with the adaptor.
Figure 7:
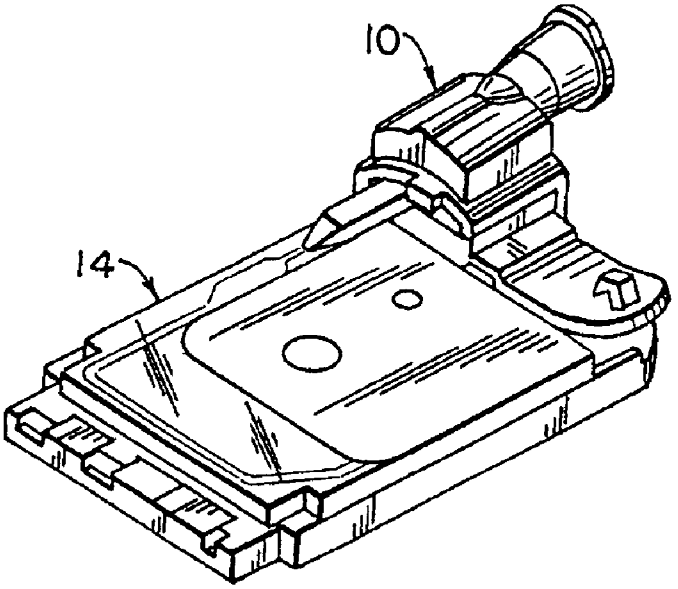
FIG. 7 is a perspective view of the adaptor mounted to the testing cartridge.
Figure 8:
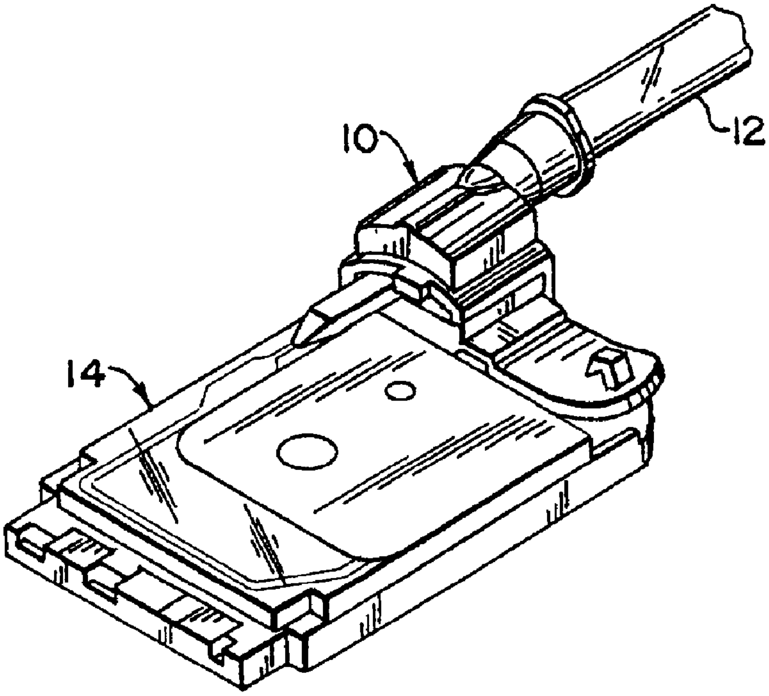
FIG. 8 is a perspective view showing the adaptor mounted to the testing cartridge and the syringe engaged in the entry port of the adaptor.

Point-of-care testing cartridge 14 is shown in FIG. 6 and may be of any of several prior art designs, including those manufactured by i-STAT Corporation, Diametrics Medical, Inc., AVL Scientific Corporation or any other such testing cartridges that are available or become available. One such testing cartridge is disclosed in U.S. Pat. No. 5,638,828, the disclosure of which is incorporated herein by reference.

Testing cartridge 14 includes a generally rectangular body 56 with a top wall 58 that has a length of approximately 1.5–2.0 inches and a width of about 1.0 inches. Body 56 further has side walls 60 and end walls 62 that define a thickness for body 56 of about 0.25 inches. A fluid reservoir 64 is formed inside body 56 of cartridge 14 and has a volume in the range of 40 $\mu$l and 125 $\mu$l. Body 56 further includes an entry port 66 that extends through top wall 58 and communicates with reservoir 64. Entry port 66 is slightly tapered from a relatively large diameter portion externally on housing 56 to a relatively smaller cross-section closer to reservoir 58. Additionally entry port 66 is spaced from one side wall 60 and one end wall 62 by a distance a. Testing cartridge 14 further includes contact pads and sensors 68 that can be placed in communication with a portable clinical analyzer for performing various point-of-care diagnostic tests on the sample of fluid in the reservoir 64 and for providing various readout data that can be used by a health care technician at the point-of-care and/or at a remote location.

Adaptor 10 is molded unitarily from a transparent plastic material and includes a mounting sleeve 70 and a Luer fitting 72. Mounting sleeve 70 includes a substantially planar bottom wall 74. The bottom wall 74 includes a top surface 76 with locking detents 78 and 80 formed thereon. Detents 78 and 80 are disposed and configured for locked engagement on testing cartridge 14 as explained further herein. Mounting sleeve 70 further includes a side wall 82 that extends orthogonally from bottom wall 74 a distance approximately equal to the height of side wall 60 on body 56 of testing cartridge 14. An end wall 84 extends orthogonally from bottom wall 74 and from side wall 82. Mounting sleeve 70 further includes a top wall 86 that extends from portions of side wall 82 and end wall 84 remote from bottom wall 74. Top wall 86 includes a concave inner surface 88 that defines a section of a cylinder generated about an axis extending parallel to side wall 82. A concave configuration of inner surface 88 is configured to permit nesting with a convex region of top wall 58 of testing cartridge 14 in proximity to entry port 66. Top wall 86 is further characterized by a locking detent 90 that projects toward bottom wall 74. Locking detent 90 is dimensioned and configured for locked engagement with corresponding structure on top wall 58 of testing cartridge 14.

Luer fitting 72 of adaptor 10 includes an inlet end 92, an outlet end 94 and a passage 96 extending between the ends. Portions of passage 96 adjacent inlet end 92 define a female Luer fitting with a conical taper for mating with a Luer tip of a syringe. Additionally, portions of passage 96 adjacent inlet end 92 are aligned substantially parallel to both top wall 86 and side wall 82. However, portions of passage 96 adjacent outlet end 94 defines a smaller cross-section than portions of passage 96 adjacent inlet end 92, and smaller than entry port 66 of testing cartridge 14. Thus, fluid flow through adaptor 10 can be controlled carefully and air in reservoir 64 can be vented easily. The ease of venting also can be controlled by varying the distance by which the outlet end 94 projects from the inner surface 88 of top wall 86, as shown by broken lines in FIG. 4. Additionally, these portions of passage 96 adjacent outlet end 94 extend orthogonally through a central portion of top wall 86. Thus, the respective inlet and outlet ends of passage 96 are substantially perpendicular to one another. Inlet end 92 of Luer fitting 72 further include lugs 98 extending outwardly thereon. Lugs 98 are dimensioned for threaded engagement with internal threads on a Luer collar of a syringe.

Syringe assembly 12 is used in a conventional manner to draw a sample of fluid from a patient. More particularly, needle assembly 36 can be mounted to Luer tip 26 of syringe body 16, and needle cannular 38 of needle assembly 36 can be inserted into a blood vessel of a patient or other source of bodily fluid for drawing a sample of blood or other such fluid. Alternatively, a blunt plastic cannula or other plastic Luer fitting can be mounted to Luer tip 26, and the distal end of the blunt plastic cannula or other fitting can be urged through the septum that seals a fitting of a fluid collection set. Still further, syringe assembly 12 can be connected directly to an arterial or venous line that had already been placed in communication with a patient. With any of these optional approaches, plunger 34 is moved proximally after accessing the supply of fluid. Proximal movement of plunger 34 draws fluid into fluid receiving chamber 24 of syringe barrel 22. The volume of fluid drawn into fluid receiving chamber 24 is in excess of the volume of fluid required for testing cartridge 14, which typically is in the range of 40 μl–125 μl. Needle assembly 36 or the blunt plastic cannula, if used, then is removed from syringe body 16 substantially in a conventional manner and is disposed of in a sharps receptacle.

Point-of-care testing cartridge 14 then is removed from the manufacturer's package, and any closure that may have been positioned over entry port 66 is rotated away from entry port 66. Adaptor 10 then is mounted to testing cartridge 14. More particularly, mounting sleeve 70 of adaptor 10 is slid onto the corner of testing cartridge 14 in proximity to entry port 66. Specifically, bottom wall 76 is slid adjacent bottom wall 59 of testing cartridge 14. Simultaneously, side wall 82 of adaptor 10 is slid adjacent side wall 60 of testing cartridge 14 and concave surface 88 of top wall 86 is slid adjacent convex portions of top wall 58 of testing cartridge 14 adjacent entry port 66. Locking detents 78, 80 and 90 of mounting sleeve 70 cause bottom wall 76 and top wall 86 to be biased away from one another. However, after full mounting on testing cartridge 14, detents 78, 80 and 90 will snap into engagement with corresponding recesses on testing cartridge 14. End wall 84 also will abut end wall 62 of testing cartridge 70 when locking detent 78, 80 and 90 snap into engagement with testing cartridge 14. Additionally, outlet end 94 of Luer fitting 72 will align with entry port 66 of testing cartridge 14 when locking detents 78, 80 and 90 are appropriately locked with testing cartridge 14. In this embodiment, the outlet end is cross-sectionally smaller than entry port 66 and top wall 86 is spaced above entry port 66. Thus air in reservoir 64 can be vented easily. In other embodiments, adaptor 10 can be dimensioned for engagement with testing cartridge 14 near entry port 66. Additionally or alternatively, an O-ring can be provided around outlet end 94. These optional designs prevent splatter, but do not permit venting of air.

Luer tip 26 of syringe assembly 12 then is inserted into passage 96 at inlet end 92 of Luer fitting 72. Thus, Luer tip 26 will be urged into fluid-tight sealing engagement with conically tapered portions at the entry end of passage 96 in Luer fitting 72 of adaptor 10. Embodiments of syringe assembly 12, such as those illustrated in the figures hereto are provided with Luer collar 30 with an array of internal threads 32. For these embodiments, syringe assembly 12 is rotated about its axis so that lugs 92 on Luer fitting 72 of adaptor 10 threadedly engage Luer collar 30.

The use of testing cartridge 14 proceeds merely by urging plunger 34 distally in syringe body 16. Movement of plunger 34 causes blood in fluid receiving chamber 24 to be urged through Luer tip 26 of syringe body 16, through passage 96 of adaptor 10 and into reservoir 64 of testing cartridge 14. Syringe assembly 12 then is separated from adaptor 10 and testing cartridge 14. A cylindrical cap then is mounted on inlet end 92 of Luer fitting 72 of adaptor 10 and testing cartridge 14 with adaptor 10 mounted thereon are inserted into communication with a portable clinical analyzer for analysis of the specimen.

While the invention has been described with respect to a preferred embodiment, it is apparent that various changes can be made without departing from the scope of the invention as defined by the claims. For example, the adaptor can be snapped on the testing cartridge at the place of manufacturing the testing cartridge and can be sold as a preassembled unit. Alternatively, the adaptor can be molded unitarily with the housing of the testing cartridge.

What is claimed is:

1. An adaptor for use with a testing cartridge and a syringe to facilitate delivery of a fluid specimen from said syringe to said testing cartridge, said testing cartridge having a bottom wall, a top wall and at least one side wall extending between said top and bottom walls, an entry port extending through said top wall for delivering the specimen to the testing cartridge, said adaptor comprising a mounting sleeve configured for slidable mounting over portions of said top and bottom wall of said testing cartridge including portions of said top wall having said entry port therein, at least one locking detent formed on said mounting sleeve for locked engagement with said testing cartridge, and a Luer filling having an outlet end extending through said mounting sleeve at a location for alignment with said entry port when said mounting sleeve is mounted on said testing cartridge, an inlet end spaced from said outlet end and a passage extending between said ends, said passage having at least one non-linear portion so that said inlet end is aligned at an angle to said outlet end, said inlet end being configured for fluid-tight mounting with said syringe.

2. The adaptor of claim 1, wherein the mounting sleeve comprises a bottom wall for slidable engagement with said bottom wall of said testing cartridge and a top wall configured for sliding engagement with said top wall of said testing cartridge, said locking detents being formed respectively on said top and bottom walls of said adaptor.

3. The adaptor of claim 2, wherein said mounting sleeve further comprises a side wall extending between said top and bottom walls and disposed for slidable engagement against said side wall of the testing cartridge.

4. The adaptor of claim 3, further comprising an end wall extending between said top and bottom walls and angularly aligned to said side wall.

5. The adaptor of claim 1, wherein portions of said passage adjacent said inlet end of said Luer fitting define a conical taper configured for mating with a Luer tip of said syringe.

6. The adaptor of claim 5, wherein portions of said Luer fitting adjacent said inlet end include a pair of projections configured for threaded engagement with a Luer collar on said syringe.

7. A adaptor for use with a testing cartridge and a syringe to facilitate delivery of a fluid specimen from said syringe to said testing cartridge, said testing cartridge having a bottom wall, a top wall and at least one side wall extending between said ton and bottom walls, an entry port extending through said top wall for delivering the specimen to the testing cartridge, said adaptor comprising a mounting sleeve configured for slidable mounting over portions of said too and bottom wall of said testing cartridge including portions of said too wall having said entry port therein, and a Luer fitting having an outlet end extending through said mounting sleeve at a location for alignment with said entry port when said mounting sleeve is mounted on said testing cartridge, an inlet end spaced from said outlet end and a passage extending between said ends, said inlet end being configured for fluid-tight mounting with said syringe, the mounting sleeve having a bottom wall for slidable engagement with said bottom wall of said testing cartridge and a too wall configured for sliding engagement with said too wall of said testing cartridge, locking detents being formed respectively on said too and bottom walls of said adaptor for locked engagement with said testing cartridge, wherein portions of said passage through said Luer fitting adjacent said inlet end of said Luer fitting are aligned substantially parallel to said bottom wall.

8. The adaptor of claim 7, wherein portions of said passage through said Luer fitting adjacent said outlet end of said Luer fitting are aligned substantially orthogonal to said bottom wall of said adaptor.

9. An adaptor for use with a testing cartridge and a syringe to facilitate delivery of a fluid specimen from said syringe to said testing cartridge, said adaptor comprising a mounting sleeve having a substantially planar bottom wall with at least one locking detent formed thereon for snapped engagement with said testing cartridge, side and end walls projecting from said bottom wall for positioning said mounting sleeve relative to said testing cartridge, a top wall extending from said side and end walls in spaced relationship to said bottom wall, a Luer fitting unitarily formed with said top wall, said Luer fitting having an inlet section with an inlet end, said inlet section being aligned substantially parallel to said bottom wall, said Luer fitting further having an outlet section with an outlet end aligned substantially orthogonally to said bottom wall, a passage extending continuously between said inlet end and said outlet end of said Luer fitting, portions of said passage adjacent said inlet end being configured for mating with a Luer tip of said syringe.

* * * * *